Figure 1:
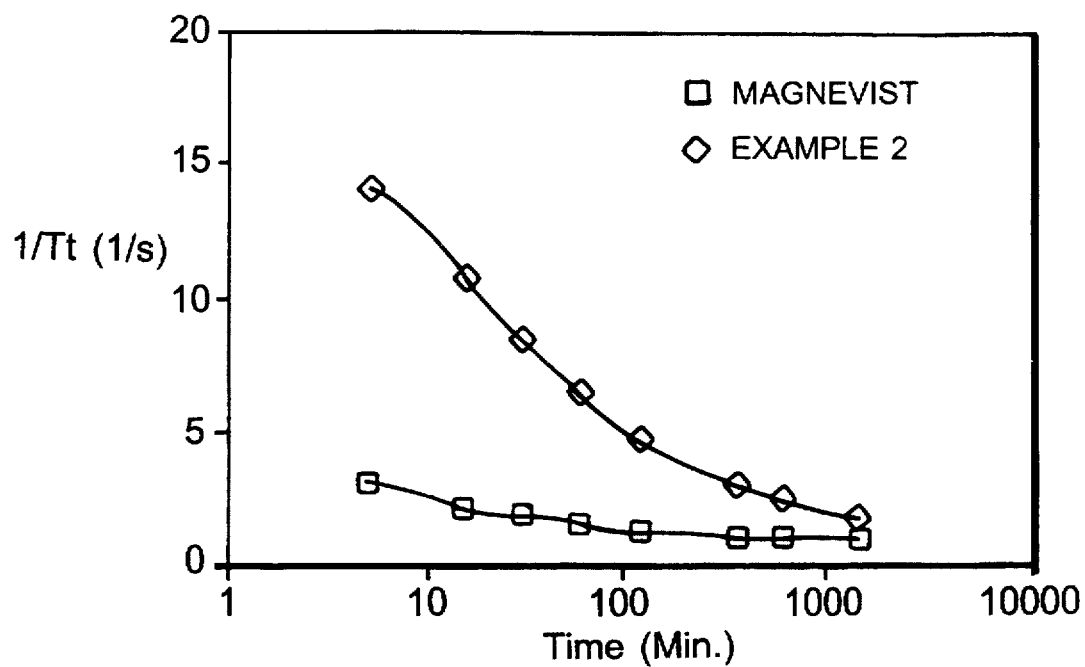

United States Patent [19]

Hollister et al.

[11] Patent Number: 5,801,228
[45] Date of Patent: Sep. 1, 1998

[54] POLYMERIC CONTRAST AGENTS FOR MEDICAL IMAGING

[75] Inventors: Kenneth Robert Hollister; Kenneth Edmund Keller; Dong Wei; Xin Peng; David Lee Ladd, all of Wayne, Pa.; Paul Mark Henrichs, Houston, Tex.; Robert Allen Snow, West Chester, Pa.

[73] Assignee: Nycomed Imaging AS, Oslo, Norway

[21] Appl. No.: 478,803

[22] Filed: Jun. 7, 1995

[51] Int. Cl.$^6$ .............................. C07F 5/00; A61K 49/00; C09F 13/00
[52] U.S. Cl. .................... 534/15; 534/16; 424/9.36; 424/9.363; 424/9.365; 556/45; 556/49
[58] Field of Search .......................... 534/10, 14, 15, 534/16; 424/1.65, 9.364, 9.365, 936, 9.363; 556/45, 49, 50

[56] References Cited

U.S. PATENT DOCUMENTS

| | | | |
|---|---|---|---|
| 4,707,453 | 11/1987 | Wagner et al. | 436/501 |
| 4,855,353 | 8/1989 | Kurami et al. | 525/54.1 |
| 5,198,208 | 3/1993 | Berg et al. | 424/1.1 |
| 5,281,704 | 1/1994 | Love et al. | 540/465 |
| 5,338,532 | 8/1994 | Tomalia et al. | 424/1.49 |
| 5,364,613 | 11/1994 | Sieving et al. | 424/9 |
| 5,466,438 | 11/1995 | Unger et al. | 424/9.365 |
| 5,466,439 | 11/1995 | Gibby et al. | 424/9.365 |
| 5,482,699 | 1/1996 | Almen et al. | 424/9.42 |
| 5,556,968 | 9/1996 | Carvalho et al. | 540/460 |

FOREIGN PATENT DOCUMENTS

| | | |
|---|---|---|
| 273274 | 1/1992 | Czechoslovakia . |
| 0485045 | 5/1990 | European Pat. Off. . |
| 0512661 | 5/1992 | European Pat. Off. . |
| 1304063 | 1/1993 | United Kingdom . |
| 90/12050 | 10/1990 | WIPO . |
| WO 92/08707 | 5/1992 | WIPO . |
| 93/06148 | 4/1993 | WIPO . |
| 93/06868 | 4/1993 | WIPO . |
| 94/08629 | 4/1994 | WIPO . |
| WO 94/09056 | 4/1994 | WIPO . |
| 95/09848 | 4/1995 | WIPO . |
| WO 95/26754 | 10/1995 | WIPO . |

OTHER PUBLICATIONS

Michiru Ueda et al., "Properties of Chelate Polymers with Ethylrnrdiamine Tetraacetic Acid Structure" Kobunshi Ronbunshu, vol. 32, No. 4, pp. 225–228, (Apr. 1975) (including translation).

Eric M. Chellquist et al., "Binding constant determination of WIN 22169, a novel polymeric ligand", Journal of Pharmaceutical & Biomedical Analysis, vol. 12, No. 8, pp. 1015–1022, 1994.

Koenig, Seymour H. et al., "Field–Cycling Relaxometry of Protein Solutions and Tissue: Implications for MRI," Progress in NMR Spectroscopy, vol. 22, Great Britain, 1990, 487–567.

Woessner, D. E., "Spin Relaxation Processes in a Two–Proton System Undergoing Anisotropic Reorientation," Journal of Chemical Physics, vol. 36, No. 1, American Institute of Physics, 1962, pp. 1–4.

Primary Examiner—John Kight
Assistant Examiner—Lara C. Kelley
Attorney, Agent, or Firm—Fish & Richardson

[57] ABSTRACT

The invention provides polymeric polychelants containing polymer repeat units of formula [L—Ch—L—B] (where Ch is a polydentate chelant moiety; L is an amide or ester linkage; B is a hydrophobic group providing a carbon chain of at least 4 carbon atoms between the L linkages it interconnects) or a salt or chelate thereof, with the proviso that where Ch is 2,5-biscarboxymethyl-2,5-diazahex-1,6-diyl, the polychelant is metallated with lanthanide or manganese ions or B provides a carbon chain of at least 10 carbon atoms between the L linkages it interconnects and their salts and chelates. The paramagnetic polychelates of the polychelants of the invention have remarkably high $R_1$ relaxivities.

19 Claims, 1 Drawing Sheet

POLYMERIC CONTRAST AGENTS FOR MEDICAL IMAGING

This invention relates to polychelant compounds and salts and metal complexes thereof, particularly polymetallated complexes useful as contrast agents for diagnostic imaging procedures, in particular magnetic resonance imaging (MRI).

In medical imaging modalities such as magnetic resonance imaging, it has become accepted practice to use contrast agents, that is to say materials which enhance the contrast between tissues or organs or between diseased and healthy tissue in the images that are generated.

In MRI, contrast agents generally achieve their contrast enhancing effect by modifying the characteristic relaxation times of the imaging nuclei (generally water protons) in the body regions into which they distribute.

Commercially available contrast agents which achieve contrast enhancement in this manner include the gadolinium chelates GdDTPA, GdDTPA-BMA and GdHP-DO3A which are available from Schering, Nycomed Imaging and Squibb under the trade marks MAGNEVIST, OMNISCAN and PROHANCE respectively.

MAGNEVIST, OMNISCAN and PROHANCE are all ECF agents, that is to say following injection into the vasculature they distribute into the extracellular fluid (ECF). Various proposals have been made in the patent and scientific literature for blood pool MRI contrast agents, compounds which following injection into the vasculature have prolonged residence time in the blood vessels before being eliminated generally via the liver or kidneys.

Included among the proposed blood pool agents have been polychelants (chelating agents capable of being metallated by a plurality of metal ions) metallated by paramagnetic transition or lanthanide metal ions. See for example WO90/12050 (Sieving), WO93/06868 (Watson), WO93/06148 (Unger), EP-A-512661 (Schering), etc.

The use of polychelants has the advantage that a plurality of contrast generating metal ions may be delivered simultaneously, thereby providing a concentrated contrast enhancing effect.

Various polychelant structures have been proposed, from simple dimers of macrocyclic chelants (see for example EP-A-485045 and WO95/09848) to starburst dendrimers carrying chelating groups at the dendrimer terminay (see for example WO93/06868). Linear polychelants have also been proposed in which the chelant group is pendent from a polymer backbone (see EP-A-512661 and WO90/12050). Other linear polychelants in which the chelant groups are incorporated within the polymer backbone have also been proposed (see WO94/08629 and WO93/06148). In the latter case, the polymers contain chelant:linker polymer repeat units and the use of hydrophilic linker groups such as polyoxaalkylene or polyazaalkylene chains has been recommended, for example by WO93/06148 and WO94/08629.

Besides serving to deliver a plurality of diagnostically effective metal ions simultaneously, the macromolecular polychelants have the further advantage, relative to simple monochelates such as GdDTPA, that their anisotropic rotational correlation time is greater, which results in increased relaxivity and thus increased efficacy in MR contrast enhancement.

Polymeric polychelants incorporating alternating chelant and hydrophobic linker moieties have also been proposed. Thus for example GB-A-1304063 (Stauffer) proposes certain EDTA derivative polymers for use as chelating agents, coagulants, flame retardants, detergent builders, etc. Amongst the EDTA derivative polymers proposed by Stauffer are polymers having hydrophobic linker groups such as hexamethylene, phenylene and 2,2-bis(1,4-phenylene)-propane. Unger in WO93/06148 moreover proposes various polymeric polychelants for use as MRI contrast agents which are based on alternating chelating moieties and hydrophilic linker moieties such as polyoxaalkylene groups. While Unger gives no examples of compounds with hydrophobic linker groups, he does make the suggestion that the monomer precursor for the hydrophilic linker (the compound of formula I) may be replaced by other listed monomers and included in his list is a small number of monomers that would give rise to hydrophobic linker groups, for example 1,4-diaminobutane, 1,4-diaminocyclohexane and 1,4-phenylenediamine. Neither Stauffer nor Unger however attach any particular benefit to the use of hydrophobic linker groups and indeed the primary teaching in Unger is towards to the use of hydrophilic linkers.

The present invention is based on the finding that surprisingly increased relaxivities are achieved using polymeric polychelants in which the linker groups joining the chelant moieties are relatively large hydrophobic groups.

Thus, viewed from one aspect, the invention provides a polymeric polychelant having polymer repeat units of formula I

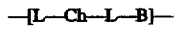 (I)

(where Ch is a polydendate chelant moiety; L is an amide or ester linkage; and B is a hydrophobic linker group providing a carbon chain of at least four carbon atoms between the L groups it interconnects) or a salt or chelate thereof, with the proviso that where Ch is 2,5-biscarboxymethyl-2,5-diazahex-1,6-diyl the polychelant is metallated with lanthanide or manganese ions or B provides a carbon chain of at least 10 carbon atoms between the L groups it interconnects. Preferably, where the linker group contains 6 or less carbons, the chelant moiety is a polyprotic species having at least 3 labile hydrogens.

The surprisingly high relaxivity achieved for the metallated polychelants of the invention is ably demonstrated by a comparison of relaxivities (at 40° C., 20 MHz) for the homologous series:

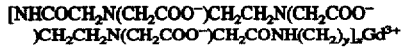

The relaxivity results for such polymers where y is from 4 to 12 are set out in Table I below.

TABLE I

| B LINKER GROUP | $r_1$ RELAXIVITY (mM$^{-1}$s$^{-1}$) |
| --- | --- |
| (CH$_2$)$_4$ | 7.98 |
| (CH$_2$)$_5$ | 8.49 |
| (CH$_2$)$_6$ | 9.5 |
| (CH$_2$)$_8$ | 12.0 |
| (CH$_2$)$_{10}$ | 16.5 |
| (CH$_2$)$_{12}$ | 20.7 |

The increase in relaxivity at magnetic field strengths relevant to MRI (e.g. 0.24 Tesla and greater) with increasing numbers of methylenes in the bridging alkylene chain in such polymeric polychelants is doubly unexpected. Firstly, the mode of attachment of chelant to linker within the polymer structure is identical in each case and accordingly one would expect that the flexibility of the chelant moieties at their points of attachment within the polymer structure, and consequently their anisotropic rotational motions, should therefore be very similar. Because the anisotropic rotational motion of the chelate complex moieties dominates the correlation time at magnetic fields strengths relevant to MRI, one would expect the relaxivities to be very similar. (See for example Woessner in J. Chem. Phys. 36:1–4(1962) and Koenig et al in Progress in NMR Spectroscopy 22:487–567(1992). Secondly, increasing the number of methylene groups within the linker moiety should result in more flexibility in the polymer chain. This would be expected to cause the anisotropic rotational correlation time to increase and as a result the relaxivity to decrease (see Woessner, Supra). Thus, as it would be expected with this homologous series that relaxivities would remain fairly constant or decrease as the number of methylene groups in the linker increases, the fact that relaxivities instead dramatically increase as the number of methylene groups increases is entirely unexpected.

The hydrophobic linker B in the compounds of the invention may have a linear, branched, cyclic or partially cyclic (e.g. -alkylene-phenylene-alkylene-) carbon skeleton which may be wholly or partially unsaturated and may optionally be substituted by hydrophobic groups, such as for example iodine or fluorine atoms. Preferably however, the hydrophobic moiety B will be linear, optionally partially unsaturated, and optionally interrupted by one or more $C_{5-7}$ homocyclic groups, e.g. cyclohexylene or phenylene. B preferably contains up to 50, especially 8 to 30, and particularly 10 to 20 carbons. The carbon chain between the L groups which is provided by hydrophobic group B is preferably 6 to 30 carbons in length and any side chain is preferably up to 6 carbons in length. Thus B may for example be in the form of a chain made up from the following units:

m units of $CH_2$ n units of CHR q units of $C_6H_4$ r units of $C_6H_{10}$, and p units of —CH═CH— where R is $C_{1-6}$ alkyl, and m, n, p, q and r are independently zero or positive integers, the sum m+n+2q+2r+2p being from 4 to 30, preferably 6 to 25 and especially 8 to 20, with n, q and r preferably being 0, 1 or 2, the product q and r preferably being 0, and p preferably being 0, 1, 2 or 3. They may thus for example be a group of formula II —(CHR)$_{n1}$(CH$_2$)$_{m1}$(CH═CH)$_p$(CH$_2$)$_{m2}$(CHR)$_{n2}$— (II)

where R is as defined above and n1, n2, m1, m2 and p are zero or positive integers, the sum n1+n2+m1+m2+2p being from 4 to 30, preferably 6 to 25 and especially preferably 8 to 20.

Particular examples of hydrophobic linker groups B include: $(CH_2)_4$, $(CH_2)_5$, $(CH_2)_6$, $(CH_2)_7$, $(CH_2)_8$, $(CH_2)_9$, $(CH_2)_{10}$, $(CH_2)_{11}$, $(CH_2)_{12}$, $(CH_2)_{13}$, $(CH_2)_{14}$, $(CH_2)_{15}$, $(CH_2)_{16}$, $(CH_2)_{17}$, $(CH_2)_{18}$, $(CH_2)_{19}$, $(CH_2)_{20}$, $CH_2CHCHCH_2$, 1,4-cyclohexylene.

The linker group B is preferably a linear alkylene chain having at least 7 carbon atoms or a linear alkenylene chain having at least 4 carbons.

The linkages L which couple the hydrophilic groups B to the chelant moieties Ch are ester or amide groups, preferably of carbon, sulphur or phosphorus oxyacids, i.e. providing a CN, SN, PN, CO, SO or PO unit within the polymer backbone. The amide nitrogens in such groups may be unsubstituted or alternatively and preferably are themselves substituted by hydrophilic or, more preferably, hydrophobic groups, such $C_{1-6}$ alkyl groups. The ester oxygen and the amide nitrogen may be attached to the chelant moiety; however it will generally be preferred that they be attached to a terminal carbon of the hydrophobic linker B as this configuration is readily achieved by condensation of a bifunctional linear compound with an optionally activated oxyacid group containing chelant, for example condensation of an α,ω-alkylenediamine with DTPA-bisanhydride.

Examples of linkages thus include —CO—O—, —O—CO—, —CO—NH—, —CO—NR—, —NH—CO—, —NR—CO—, —PO$_3$H—O—.

The chelant moiety in the polymeric polychelants of the invention may be any chelant group capable of stably binding paramagnetic metal ions. Many suitable chelating species have been described in the patent and scientific literature, especially that relating to metal chelate MRI contrast agents and the reader is referred to the patent publications of Nycomed Imaging, Nycomed Salutar, Sterling Winthrop, Schering, Squibb, Malinckrodt, Bracco and Guerbet. Particularly preferably, the chelating moiety will be the residue of a linear, branched or macrocyclic poly-N-(oxyacid-methyl) polyazaalkane, such as EDTA, DTPA, DOTA, DO3A, DOXA and TTHA. Thus the chelating moiety may for example be of formula III (X—CHR$_1$CHR$_1$)$_k$X (III)

where $R_1$ is hydrogen or optionally hydroxy or alkoxy substituted alkyl or a bond or an alkylene group linked to linkage L, or two $R_1$ groups together may represent an optionally aza or oxa substituted $C_{4-6}$ alkylene bridge; k is 1, 2, 3, 4, 5 or 6, preferably 2 or 3; each X independently is O or NR$_2$ or a bond to the nitrogen of an amide linkage L, at least two X groups being NR$_2$; each $R_2$ independently is a hydrogen atom or an alkyl group optionally substituted by hydroxy, alkoxy or COZ, POZ$_2$, SO$_2$Z, CON(R$_3$)$_2$, or linked to a linkage L, or two R$_2$ groups together represent a group CHR$_1$CHR$_1$, at least two R$_2$ groups representing COZ, POZ$_2$, SO$_2$Z or CON(R$_3$)$_2$ substituted alkyl groups; Z is a group OR$_3$ or N(R$_3$)$_2$; and R$_3$ is hydrogen or optionally hydroxylated alkyl; with two of X, R$_1$ and R$_2$ providing bonds to linkages L.

As mentioned above, such chelant moieties are well known from the literature relating to metal chelate MRI contrast agents.

Preferred as chelating moieties Ch, are groups having the structures

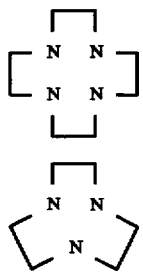

-continued

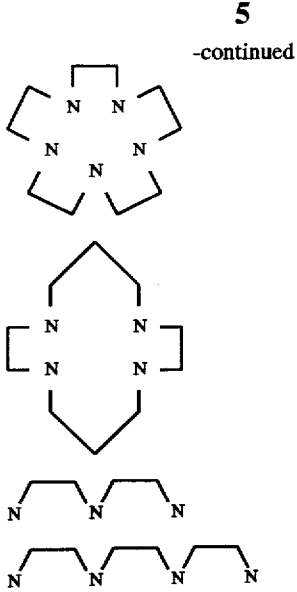

where the carbon skeletons are unsubstituted, two nitrogens carry methylene groups linked to L linkages, and the remaining nitrogens carry oxyacid-methyl groups or amides or esters thereof, preferably carboxymethyl or phosphonomethyl groups.

The compounds of the invention are polymeric, containing [L—Ch—L—B] polymer repeat units. The overall molecular weight of the polymer is conveniently in the range $10^3$ to $10^6$ D preferably 5 to 200 kD, and especially 14 to 80 kD.

The polymers of the invention may include further structural units besides the [L—Ch—L—B] repeat units, and in particular the inclusion of a relatively low proportion of hydrophilic polymer segments, either as pendent groups or as components of the polymer backbone, may be advantageous, for example in terms of prolonging blood pool residence times. Groups that may be appended or incorporated this way include in particular polyazaalkylene and more especially polyoxaalkylene chains, in particular polyethyleneoxy or polypropyleneoxy groups, e.g. PEG (polyethyleneglycol) groups. Such groups can be pendent from or incorporated within the polymer skeleton and advantageously make up to about 15% by weight of the polymer. Incorporation of such hydrophilic chains may be effected by conventional techniques, see for example WO93/06148 (Unger) and WO94/08629.

Such hydrophilic chains act as biodistribution modifiers for the polymeric compounds. Other biodistribution modifiers may also be conjugated to the polymeric compounds in order to target the polymer to particular body tissues or sites following administration. In this regard, particular mention may be made of macromolecules, biomolecules and macrostructures.

Examples of macromolecules, biomolecules and macrostructures to which the polymeric chelant may be conjugated include polymers (such as polylysine), polysaccharides, proteins, antibodies or fragments thereof (especially monoclonal antibodies or fragments such as Fab fragments), glycoproteins, proteoglycans, peptides, hormones, steroids, cell adhesion molecules, etc. In this way, for example, tumour-targeting polymeric polychelants may be produced. Conjugation of the polychelants of the invention to biodistribution modifying agents may be achieved by conventional methods and has been widely described in the MRI contrast agent literature, for example in WO90/12050, EP-A-512661, WO95/09848, etc.

The polymeric polychelants of the invention are primarily proposed for use as MR contrast agents for which use they will be metallated by paramagnetic metal ions or polyatomic cluster ions (e.g. polyoxoanion and their sulphur analogues), for example transition metal or lanthanide metal ions. The polychelant compounds of the invention may however also be used to carry other metal ions for use in different diagnostic imaging modalities or in therapy.

Especially preferred are polychelates of metals with atomic numbers 20 to 32, 42 to 44, 49 and 57 to 83, especially Gd, Dy, Mn and Yb.

For use as MR diagnostics contrast agents, the chelated metal species is particularly suitably a transition metal or a lanthanide, preferably having an atomic number of 21 to 29, 42, 44 or 57 to 71. Metal chelates in which the metal species is Eu, Gd, Dy, Ho, Cr, Mn or Fe are especially preferred and chelates multiply metallated with $Gd^{3+}$, $Mn^{2+}$ or $Dy^{3+}$ are particularly preferred.

For use as contrast agents in MRI, the paramagnetic metal species is conveniently non-radioactive as radioactivity is a characteristic which is neither required nor desirable for MR diagnostic contrast agents.

For use as X-ray or ultrasound contrast agents, the chelated metals species is preferably a heavy metals species, for example a non-radioactive metal with an atomic number greater than 37, preferably greater than 50, for example $Dy^{3+}$.

For use in scintigraphy, or radiotherapy, the chelated metal species must of course be radioactive and any conventional complexable radioactive metal isotope, such as $^{99m}Tc$, $^{67}Ga$ or $^{111}In$ for example may be used. For radiotherapy, the chelating agent may be in the form of a metal chelate with for example $^{153}Sm$, $^{67}Cu$ or $^{90}Y$.

For use in detoxication of heavy metals, the polychelant is desirably in salt form with a physiologically acceptable counterion, for example sodium, calcium, ammonium, zinc or meglumine, for example as the sodium salt of a polycalcium chelate complex.

Where the polychelates are ionic, for example where the deprotonated chelant moiety carries a greater negative charge than is required to balance the positive charge of the complex metal ions, the compounds may be presented in the form of salts. In such cases, the counterions will preferably be physiologically tolerable organic or inorganic ions, such as ammonium, substituted ammonium, alkaline metal or alkaline earth metal. In this regard, meglumine salts are particularly preferred.

The polymeric compounds of the invention may be prepared and metallated by conventional polymerization and metallation techniques and these form a further aspect of the invention. Viewed from this aspect, the invention provides a process for the preparation of the compounds of the invention, said process comprising at least one of the following steps:

(a) copolymerising a difunctional compound of formula IV $$Y_1—B—Y_1 \qquad (IV)$$

with a difunctional compound of formula V $$Y_2—Ch—Y_2 \qquad (V)$$

where B and Ch are as defined above and $Y_1$ and $Y_2$ are groups inter-reactive to produce an amide or ester linkage;

(b) metallating or transmetallating a polymeric polychelant having polymer repeat units of formula I as defined above;

(c) conjugating a biotargeting group to a polymeric polychelant having polymer repeat units of formula I as defined above; and (d) copolymerising difunctional compounds of formulae IV and V together with a further monomer of formula VI

   (VI)

where $Y_1$ is as hereinbefore defined and Hp is a linker group, for example a polyoxaalkylene species (such as group of formula $(CH_2)_2(OCH_2CH_2)_x$), preferably one having a molecular weight of 400 to 5000.

In the polymerization reactions of steps (a) and (d) above, $Y_1$ is preferably a hydroxyl or more preferably a primary or secondary amine group and $Y_2$ is preferably an optionally activated oxyacid, as for example an acid chloride or more preferably an acid anhydride group.

Difunctional reagents of formulae IV and VI are known or may be prepared using conventional chemical techniques. Longer hydrophobic components for compounds of formula IV may be built up from shorter components.

The molecular weight of the polymer product may be regulated by appropriate selection of the polymerization reaction parameters (i.e. temperature, solvent, concentration, monomer ratio, catalyst bases etc.).

The metallation of the polychelant may be achieved using conventional techniques, either by direct metallation or by transmetallation, for example reacting the polychelant in solution with the soluble salt of the metal, for example a chloride salt, or with an oxide of the metal.

The polychelants of the invention may, as indicated above, be used as diagnostic imaging agents or in therapy.

Thus, viewed from a further aspect, the present invention provides a diagnostic or therapeutic agent comprising a polymeric polychelate according to the invention, together with at least one pharmaceutical or veterinary carrier or excipient. Viewed from a further aspect, the invention provides a detoxification agent comprising a polychelant according to the invention in the form of a weak complex or salt with a physiologically acceptable counterion, together with at least one pharmaceutical or veterinary carrier or excipient.

Viewed from a yet further aspect, the invention provides a method of generating enhanced images of the human or non-human, preferably mammalian, animal body, which method comprises administering to said body a diagnostically effective amount of a polychelant according to the invention polymetallated with a diagnostically effective metal, and generating an image of at least part of said body to which said metallated polychelant distributes.

Viewed from another aspect, the present invention also provides a method of radiotherapy practised on the human or non-human animal, preferably mammalian, body, which method comprises administering to said body an effective amount of a chelate of a radioactive metal species with a polychelant according to the invention.

Viewed from yet another aspect, the present invention provides a method of heavy metal detoxification practised on the human or non-human animal, preferably mammalian, body, which method comprises administering to said body an effective amount of a polychelant according to the invention or a physiologically tolerable salt or weak complex thereof.

Viewed from a yet still further aspect, the present invention provides the use of a polymeric compound according to the invention for the manufacture of diagnostic or therapeutic agents.

The diagnostic and therapeutic agents of the present invention may be formulated together with conventional pharmaceutical or veterinary formulation aids, for example stabilisers, antioxidants, osmolality adjusting agents, buffers, pH adjusting-agents, chelants, calcium salts or complexes, etc. and may be in a form suitable for parenteral or enteral administration, for example injection or infusion or administration directly into a body cavity having an external escape duct. Thus the agent of the present invention may be in a conventional pharmaceutical administration form such as a tablet, capsule, powder, solution, suspension, dispersion, syrup, suppository, etc.; however, solutions, suspensions and dispersions in physiologically acceptable carrier media, for example water for injections, will generally be preferred.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

If the compounds are to be formulated in suspension form, for example in water or physiological saline for oral administration, a small amount of soluble chelates may be mixed with one or more of the inactive ingredients traditionally present in oral solutions and/or surfactants and/or aromatics for flavouring.

For MRI and X-ray imaging, the most preferred mode for administering the metallated polychelants of the invention will be parenteral, for example intravenous, administration. Parenterally adminsterable forms, for example intravenous solutions, should be sterile and free from physiologically unacceptable agents, and should have low osmolality to minimize irritation or other adverse effects on administration, and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such are described in Remmington's Pharmaceutical Sciences, 15th Edition, Easton:Mack Publishing Company, pages 1405-1412 and 1461-1487(1975) and The National Formulary XIV, 14th Edition, Washington, American Pharmaceutical Association (1975). The solutions can contain preservatives, antimicrobial agents, buffers and antioxidants conventially used for parenteral solutions, as well as excipients and other additives which are compatible with the polymeric agents and which will not interfere with the manufacture, storage or the use of the products.

Where the diagnostic or therapeutic agent comprises a chelate or salt of a toxic metal species, for example a heavy metal ion, it may be desirable to include within the formulation a slight excess of the chelating agent, for example as discussed by Schering in DE-A-3640708, or more preferably a slight excess of the calcium salt of such a chelating agent.

For MR diagnostic examination, the diagnostic agent of the present invention, if in solution, suspension or dispersion form, will generally contain the metal chelate at a concentration in the range 1 micromol to 1.5 mol per liter, preferably 0.1 to 700 mM. The diagnostic agent however may be supplied in a more concentrated form for dilution prior to administration. The diagnostic agent of the invention may conventionally be administered in amounts of from $10^{-3}$ to 3 mmol of the metal species per kilogram of bodyweight, e.g. about 0.1 mmol lanthanide (e.g. Dy or Gd) /kg bodyweight.

For X-ray examination, the dose of the contrast agent should generally be higher and for scintographic examination the dose should generally be lower than for MR examination. For radiotherapy and detoxification, conventional dosages may be used.

The present invention will now be illustrated further by the following non-limiting Examples.

EXAMPLE 1

1,6-Hexanediamine:DTPA Polymer

To a solution of 2.97 g (25.5 mmol) of 1,6-hexanediamine in 45.1 ml of dimethylsulphoxide were added 11.08 ml (79.5 mmol) of triethylamine and 9.45 g (31.8 mmol) of diethylenetriaminepentaacetic dianhydride with vigorous stirring. The resulting reaction mixture was stirred at ambient temperature for 28 hours to give a homogeneous solution, following which it was diluted to approximately 1% solids content with water and diafiltered for 5 turnovers using a nominal 10000 molecular weight cutoff, spiral wound, polysulphone diafiltration membrane. The resulting aqueous retentate was then freeze-dried to yield a hygroscopic white solid.

Yield 7.6 g.

EXAMPLE 2

Gd (III) Complex of 1,6-Hexanediamine:DTPA Polymer 15.0 g of the polymer of Example 1 was dissolved in 600 ml of deionized water and stirred at moderate speed as it was slowly treated with a 5% aqueous solution of gadolinium (III) chloride hexahydrate. The addition was continued until a small test sample, dripped into PAR test reagent, caused a colour change from pale yellow to deep yellow. The PAR test reagent had been prepared previously by sonicating a mixture of 40 ml deionized water, 20 ml of trace metal grade ammonium hydroxide, and 0.005 g of 4-(2-pyridylazo) resorcinol for one minute. Following sonication, it was treated with 5.7 ml of trace metal grade acetic acid, allowed to cool to ambient temperature, and diluted to 100.0 ml with additional deionized water.

Upon observing the colour change in the PAR reagent, the polymer complex was diafiltered as in Example 1 for 6 turnovers, following which the pH was adjusted to 6.5 with 3.0M NaOH. The product was then freeze-dried to produce a fluffy white solid.

Yield 6.6 g.

Weight average molecular weight: 28100.

Number average molecular weight: 20400.

Polymer dispersity: 1.38.

Gadolinium Content: 21.75 weight percent bound gadolinium and 0.009 weight percent free gadolinium.

EXAMPLE 3

1,8-Octanediamine:DTPA Polymer

The title compound was produced analogously to Example 1 using 1,8-octanediamine.

EXAMPLE 4

Gd (III) Complex of 1,8-Octanediamine:DTPA Polymer

The title compound was produced analogously to Example 4 using the polymer of Example 3.

Weight average molecular weight: 16200.

Number average molecular weight: 10100.

Polymer dispersity: 1.6.

Gadolinium Content: 19.95 percent gadolinium by weight.

EXAMPLE 5

1,10-Decanediamine:DTPA Polymer

To a solution of 1.78 g (10.3 mmol) of 1,10-diaminodecane in 45.4 ml of dimethylsulphoxide were added 4.44 ml (31.8 mmol) of triethylamine and 3.78 g (10.6 mmol) of diethylenetriaminepentaacetic dianhydride with vigorous stirring. The resulting reaction mixture was stirred at ambient temperature for 17 hours to give a homogenous solution, following which it was diluted to approximately 1% solids with water and diafiltered for 8 turnovers using a nominal 10000 molecular weight cutoff, spiral wound, polysulphone diafiltration membrane. The resulting aqueous retentate was then freeze-dried yielding a hygroscopic white solid.

Yield 3.1 g.

EXAMPLE 6

Gd (III) Complex of 1,10-Decanediamine:DTPA Polymer 2.2 g of the polymer of Example 5 was dissolved in 220 ml of dionized water and stirred at moderate speed as it was slowly treated with a 5% aqueous solution of gadolinium (III) chloride hexahydrate. The addition was continued until a small test sample, dripped into PAR test reagent, caused a colour change from pale yellow to deep yellow. The PAR test reagent had been prepared previously as described in Example 2.

Upon observing the colour change in the PAR reagent, the polymer complex was diafiltered as in Example 5 through a further 6 turnovers, following which the pH was adjusted to 6.5 with 3.0M NaOH. The product was then freeze-dried to produce a fluffy white solid.

Yield 1.64 g.

Weight average molecular weight: 10300.

Number average molecular weight: 6800.

Polymer dispersity: 1.52.

Gadolinium Content: 19.92 percent by weight bound gadolinium and less than 0.001 percent by weight free gadolinium.

EXAMPLE 7

1,12-Dodecanediamine:DTPA Polymer

The title product was prepared analogously to the compound of Example 1 using 1,12-dodecanediamine as the starting diamine.

EXAMPLE 8

Gd (III) Complex of 1,12-Dodecanediamine:DTPA Polymer

The Gd (III) complex of the polymer of Example 7 was prepared analogously to the Gd (III) complex of Example 2.

Weight average molecular weight: 15700.
Number average molecular weight: 8700.
Polymer dispersity: 1.8.
Gadolinium Content: 20.06 percent by weight.

EXAMPLE 9

The Gd (III) complex of 1,6-hexanediamine:DTPA polymer, with molecular weights 9 kD, 14 kD, 18 kD, was compared to GdTPA (Magnevist) for its retention in blood in rabbits. Each rabbit was injected with one of the contrast agents at a level of 0.1 mmol Gd per kg bodyweight. Blood samples were withdrawn at various time points from each animal, and the longitudinal relaxation rate ($r_1$ in $mM^{-1}s^{-1}$) was measured at a temperature of 40° C. and a magnetic field strength 0.47 Tesla. The results are set out in FIG. 1 hereto. This ex vivo experiment directly correlates to the in vivo magnetic resonance imaging study described in Example 10 below demonstrating magnetic resonance imaging enhancement as a function of time.

EXAMPLE 10

Figure 2:
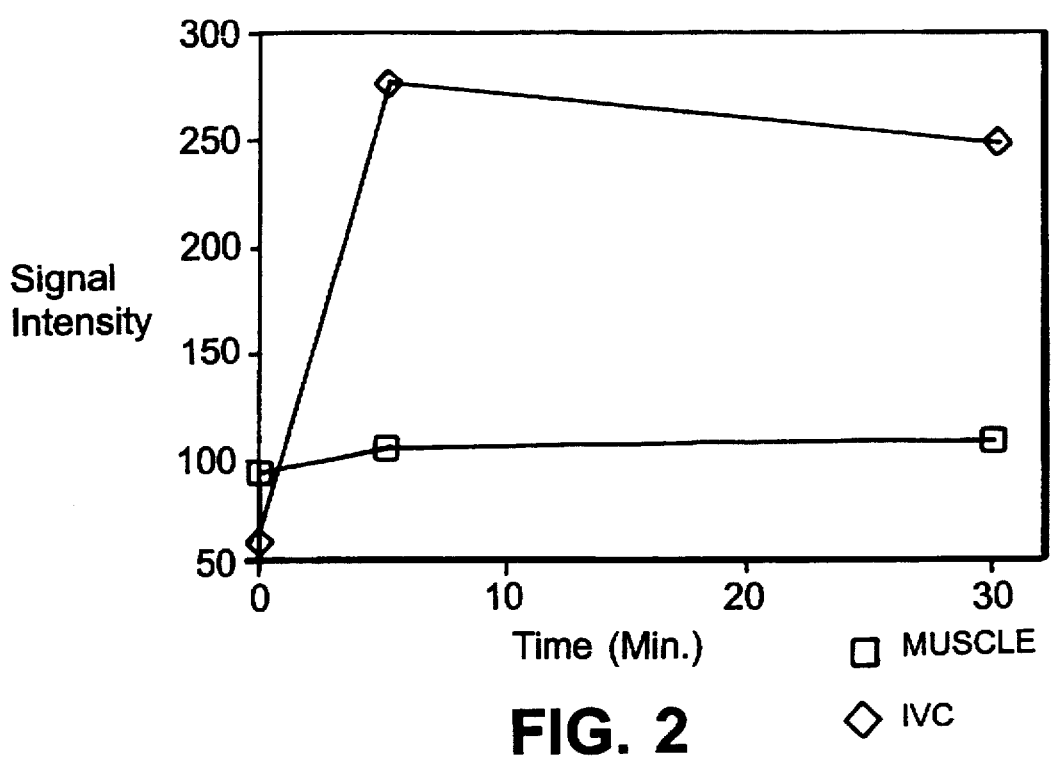

The Gd (III) complexes of 1,6-hexanediamine:DTPA polymer used in Example 9 were also used in an imaging study, again in rabbits. Each rabbit was injected with one of the contrast agents at a level of 0.1 mmol Gd per kg of bodyweight. Magnetic resonance imaging of muscle and of the inferior vena cava was done on each animal at various time points. The magnetic field strength used was 1.5 Tesla. The imaging results are set out in FIG. 2 of the accompanying drawings.

EXAMPLE 11

1,4-Butanediamine: DTPA Polymer

The title compound was prepared analogously to the polymer described in Example 1 except that the diamine employed was 1,4-butanediamine.

Weight average molecular weight: 15,000

EXAMPLE 12

Gd(III) Complex of 1,4-butanediamine: DTPA Polymer

The gadolinium complex of the polymer of Example 11 was prepared and purified in a similar manner to that described in Example 2.

Weight average molecular weight: 8,000
Number average molecular weight: 5,700
Polymer dispersity: 1.41
Gd content: 26.2% (by weight)

EXAMPLE 13

1,5-Pentanediamine: DTPA Polymer

The title compound was prepared analogously to the polymer described in Example 1 except that the diamine employed was 1,5-pentanediamine.

Weight average molecular weight: 12,700
Number average molecular weight: 6,900
Polymer dispersity: 2.31

EXAMPLE 14

Gd(III) Complex of 1,5-Pentanediamine: DTPA Polymer

The gadolinium complex of the polymer of Example 13 was prepared and purified in a similar manner to that described in Example 2.

Weight average molecular weight: 8,300
Number average molecular weight: 5,600
Polymer dispersity: 1.48
Gd content: 25.60% (by weight)

EXAMPLE 15

N,N'-Dimethyl-1,6-Hexanediamine: DTPA Polymer

The title compound was prepared analogously to the polymer described in Example 1 except that the diamine employed was N,N'-dimethyl-1,6-hexanediamine.

Weight average molecular weight: 28,600
Number average molecular weight: 11,800
Polymer dispersity: 2.41

EXAMPLE 16

Gd(III) Complex of N,N'-Dimethyl-1,6-Hexanediamine: DTPA Polymer

The gadolinium complex of the polymer of Example 15 was prepared and purified in a similar manner to that described in Example 2.

Weight average molecular weight: 16,700
Number average molecular weight: 9,200
Polymer dispersity: 1.81
Gd content: 26.2% (by weight)

EXAMPLE 17

Trans-1,2-Diaminocyclohexane: DTPA Polymer

The title compound was prepared analogously to the polymer described in Example 1 except that the diamine employed was trans-1,2-diaminocyclohexane.

Weight average molecular weight: 8,300
Number average molecular weight: 5,900
Polymer dispersity: 1.40

EXAMPLE 18

Gd(III) Complex of Trans-1,2-Diaminocyclohexane

The gadolinium complex of the polymer of Example 17 was prepared and purified in a similar manner to that described in Example 2.

Weight average molecular weight: 5,400
Number average molecular weight: 4,000
Polymer dispersity: 1.37
Gd content: 24.94% (by weight)

EXAMPLE 19

N,N'-Diethyl-2-butene-1,4-diamine: DTPA Polymer

The title compound was prepared analogously to the polymer described in Example 1 except that the diamine employed was N,N'-diethyl-2-butene-1,4-diamine.

Weight average molecular weight: 16,100
Number average molecular weight: 6,600
Polymer dispersity: 2.45

EXAMPLE 20

Gd(III) Complex of N,N'-Diethyl-2-butene-1,4-diamine

The gadolinium complex of the polymer of Example 19 was prepared and purified in a similar manner to that described in Example 2.

Weight average molecular weight: 16,100
Number average molecular weight: 11,400
Polymer dispersity: 1.41
Gd content: 21.16% (by weight)

EXAMPLE 21

The longitudinal proton relaxivity for compounds according to the invention ($R_1$ in $mM^{-1}s^{-1}$) was measured at a proton Larmor frequency of 20 MHz and a temperature of 40° C. in aqueous solution. The results are set out in Table II below.

TABLE II

| EXAMPLE NO. | RELAXIVITY $(R_1)mM^{-1}s^{-1}$ |
|---|---|
| 2 | 9.5 |
| 4 | 12.0 |
| 6 | 16.5 |
| 8 | 20.7 |
| 12 | 7.98 |
| 14 | 8.49 |
| 16 | 9.5 |
| 18 | 11.7 |
| 20 | 13.7 |

We claim:

1. A polymeric polychelant having polymer repeat units of formula I $$-(L-Ch-L-B)- \quad (I)$$

where Ch is a polydentate chelant moiety; L is an amide or ester linkage; B is a hydrophobic group providing a carbon chain of 6 to 30 carbon atoms between the L linkages it interconnects, or a salt or chelate thereof, metallated by paramagnetic lanthanide or manganese ions.

2. A polymeric compound as claimed in claim 1 polymetallated by paramagnetic metal ions.

3. A polymeric compound as claimed in claim 1 polymetallated by gadolinium or dysprosium ions.

4. A polymeric compound as claimed in claim 1 wherein B contains up to 50 carbon atoms.

5. A polymeric compound as claimed in claim 1 wherein B provides a linking chain made up of the following units:
m $CH_2$ units, n CHR units, q $C_6H_4$ units, r $C_6H_{10}$ units and p CH=CH units,
where R is $C_{1-6}$ alkyl, m, n, p, q and r are independently zero or positive integers, and the sum n+m+2q+2r+2p is up to 30.

6. A polymeric compound as claimed in any one of the preceding claims wherein B is a group of formula $$-(CHR)_{n1}(CH_2)_{m1}(CH=CH)_p(CH_2)_{m2}(CHR)_{n2}-$$

where R is $C_{1-6}$ alkyl, n1, n2, m1, m2 and p are zero or positive integers, and the sum n1+m1+n2+m2+2p is up to 30.

7. A polymeric compound as claimed in any one of the preceding claims wherein B is a linear alkylene group having at least 7 carbon atoms or a linear alkenylene group.

8. A polymeric compound as claimed in any one of the preceding claims wherein B is a linear $C_{8-16}$ polymethylene group.

9. A polymeric compound as claimed in claim 1 wherein L is a —CO—O—, —CO—NH— or —CONR— group wherein R is $C_{16}$ alkyl.

10. A polymeric compound as claimed in claim 1 wherein Ch is the residue of a linear, branched or cyclic poly-N-(oxyacid-methyl)polyazaalkane.

11. A polymeric compound as claimed in claim 11 wherein Ch has one of the following structures:

where the carbon skeleton is unsubstituted, 2 nitrogens carry methylene groups linked to L groups, and the remaining nitrogens carry oxyacid-methyl groups or amides or esters thereof.

12. A polymeric compound as claimed in claim 11 wherein Ch is 2,5,8-triaza-2,5,8-triscarboxymethyl-nonan-1,9-diyl.

13. A polymeric compound as claimed in claim 1 having a molecular weight of from 5 kD to 1000 kD.

14. A polymeric compound as claimed in claim 1 having a molecular weight of from 14 kD to 50 kD.

15. A polymeric compound as claimed in claim 1 having incorporated in or attached to the polymer backbone a biodistribution modifying moiety.

16. A therapeutic or diagnostic composition comprising a polymeric compound as claimed in claim 1 together with a pharmaceutical or veterinary carrier or excipient.

17. A process for preparation of a compound as claimed in claim 1, said process comprising at least one of the following steps:

(a) copolymerising a difunctional compound of formula IV $$Y_1-B-Y_1 \quad (IV)$$

with a difunctional compound of formula V $$Y_2-Ch-Y_2 \quad (V)$$

where B and Ch are as defined in claim 1 and $Y_1$ and $Y_2$ are groups inter-reactive to produce an amide or ester linkage;

(b) metallating or transmetallating a polymeric polychelant having polymer repeat units of formula I;

(c) conjugating a biotargeting group to a polymeric polychelant having polymer repeat units of formula I; and (d) copolymerising difunctional compounds of formulae IV and V together with a further monomer of formula VI

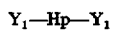 (VI)

where $Y_1$ is as hereinbefore defined and Hp is a linker group.

18. A polymeric compound according to claim 1 where Ch is 2,5-biscarboxymethyl-2,5-diazahex-1,6-diyl, and B provides a carbon chain of at least 10 carbon atoms between the L linkages it interconnects.

19. A polymeric polychelant having polymer repeat units of formula I

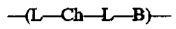 (I)

where Ch is 2,5-biscarboxymethyl-2,5-diazahex-1,6-diyl; L is an amide or ester linkage; and B is a hydrophobic group providing a carbon chain of 10 to 30 carbon atoms between the L linkages it interconnects, or a salt or chelate thereof.

* * * * *